United States Patent [19]

Komerska et al.

[11] Patent Number: 4,943,462
[45] Date of Patent: Jul. 24, 1990

[54] NAIL TREATMENT DEVICE

[75] Inventors: James Komerska, Chalfont; George Petito, Bethlehem; Borys Rybalka, Philadelphia, all of Pa.

[73] Assignee: Semex Medical, Inc., Malvern, Pa.

[21] Appl. No.: 297,576

[22] Filed: Jan. 17, 1989

[51] Int. Cl.$^5$ .................. B32B 9/02; B32B 27/04; B32B 27/08

[52] U.S. Cl. .................. 428/42; 132/73; 132/320; 424/61; 428/343; 428/355

[58] Field of Search .................. 424/61; 428/343, 355, 428/42, 79; 132/73, 75, 285, 320

[56] References Cited

U.S. PATENT DOCUMENTS

| | | | |
|---|---|---|---|
| 136,030 | 7/1943 | Belmonte et al. | |
| 2,413,537 | 12/1946 | Aberbach | 41/33 |
| 2,581,982 | 1/1952 | Terry | 428/42 |
| 3,483,289 | 12/1969 | Michaelson | 132/73 |
| 3,645,835 | 2/1972 | Hodgson | 132/73 |
| 3,875,950 | 4/1975 | Gens | 132/73 |
| 3,967,631 | 7/1976 | Kosal | 132/73 |
| 4,267,852 | 5/1981 | Hullinger | 132/73 |
| 4,441,487 | 4/1984 | Daugherty et al. | 128/24.2 |
| 4,446,965 | 5/1984 | Montiel | 206/205 |
| 4,530,828 | 7/1985 | Smith | 424/61 |
| 4,689,217 | 8/1987 | Restaino | 424/61 |
| 4,690,817 | 9/1987 | Davis | 424/61 |
| 4,824,662 | 4/1989 | Hofmann | 424/61 |

OTHER PUBLICATIONS

"Effects of phospholipids and water on brittleness of nails," Principles of Cosmetics for the Dermatologist, pp. 175–180 (1980).

"Contemporary Polymer Chemistry," Allcock, H. R. et al., Prentice-Hall, Inc., N.J., pp. 529–531 (1981).

*Primary Examiner*—George F. Lesmes
*Assistant Examiner*—J. Davis
*Attorney, Agent, or Firm*—Webb, Burden Ziesenheim & Webb

[57] ABSTRACT

The present invention is a nail hydration device in which a substrate sheet or film, suitable for application to the fingernail or toenail surface, includes a moisturizing constituent for hydrating the nail material. Preferably, the film is a polymeric film, more preferably a moisture vapor permeable polymeric film, adjacent to which is incorporated an aqueous phospholipid composition, an adhesive layer, and optional hydrolyzed animal protein (gelatin, collagen, etc.). The most preferred aqueous phospholipid composition contains water and soya phospholipids such as, for example, an aqueous soya lecithin emulsion. Typically, the aqueous phospholipid composition is dispersed within the adhesive layer. The films or tapes, which may be backed with a release liner and/or precut in the appropriate shapes, are applied to the exposed fingernails or toenails to hydrate and otherwise treat the nail material to prevent nail brittleness. The films or tapes may be applied periodically on a nightly (i.e., or every-other-night basis) in a program for minimizing nail fracture or other damage.

12 Claims, 1 Drawing Sheet

NAIL TREATMENT DEVICE

FIELD OF THE INVENTION

The present nail treatment device provides hydration to human fingernails and toenails, to enhance the manicure thereof.

BACKGROUND OF THE INVENTION

The manicurist's art is an ancient profession; manicures and pedicures appear in the records and artwork of even the earliest civilizations. Current techniques in manicure treatments are often particularly elaborate, and include acrylic copolymerization of the nail and nail bed, dietary supplements including specialized amino acids and polypeptides, not to mention various coating and strengthening compositions worn beneath nail polish or other decorative nail coatings. The predominant goal of these nail-treating protocols is the prevention of brittleness in the keratinous matrix of the nail, inasmuch as it is brittleness which leads to the unwanted chipping and breakage which thwart the practical and cosmetic advantages of a satisfactory manicure. Needless to say, dietary supplements and acrylic or other polymerizations are drastic, expensive measures when nail care is seen in perspective as only one of many aspects of essential grooming. Accordingly, a need remains for a means to prevent brittleness in human fingernails and toenails, for maximized cosmetic integrity, which is effective, low cost, easy to implement, and readily available.

SUMMARY OF THE INVENTION

In order to meet this need, the present invention is a nail hydration device in which a substrate sheet or film, suitable for application to the fingernail or toenail surface, includes a moisturizing constituent for hydrating the nail material. Preferably, the film is a polymeric film, more preferably a moisture vapor permeable polymeric film, adjacent to which is incorporated an aqueous phospholipid composition, an adhesive layer, and optional hydrolyzed animal protein (gelatin, collagen, etc.). The most preferred aqueous phospholipid composition contains water and soya phospholipids such as, for example, an aqueous soya lecithin emulsion. Typically, the aqueous phospholipid composition is dispersed within the adhesive layer. The films or tapes, which may be backed with a release liner and/or precut in the appropriate shapes, are applied to the exposed fingernails or toenails to hydrate and otherwise treat the nail material to prevent nail brittleness. The films or tapes may be applied periodically on a nightly (i.e., or every-other-night basis) in a program for minimizing nail fracture or other damage.

DETAILED DESCRIPTION OF THE INVENTION

Generally, the invention is a substrate sheet, i.e., film or tape, for application to a fingernail or toenail, which ensures adequate hydration of the nail for the purpose of avoiding nail brittleness or other cosmetic integrity loss. Nail application may be made nightly, every other night, or at any convenient times, periodic or otherwise.

The present films or tapes are generally those which apply a moisturizing composition to the nail surface, and preferably the films or tapes comprise a polymeric film—more preferably a moisture vapor permeable polymeric film—adjacent to which is incorporated an aqueous phospholipid composition, an adhesive composition, and optional hydrolyzed animal protein. The aqueous phospholipid composition most preferred includes aqueous soya phospholipids, i.e., an aqueous soya lecithin emulsion. Typically, the aqueous phospholipid composition is dispersed within a layer of the adhesive composition. The films or tapes are typically mounted on an appropriate release liner and are precut in appropriate fingernail or toenail shapes for application.

Figure 1:
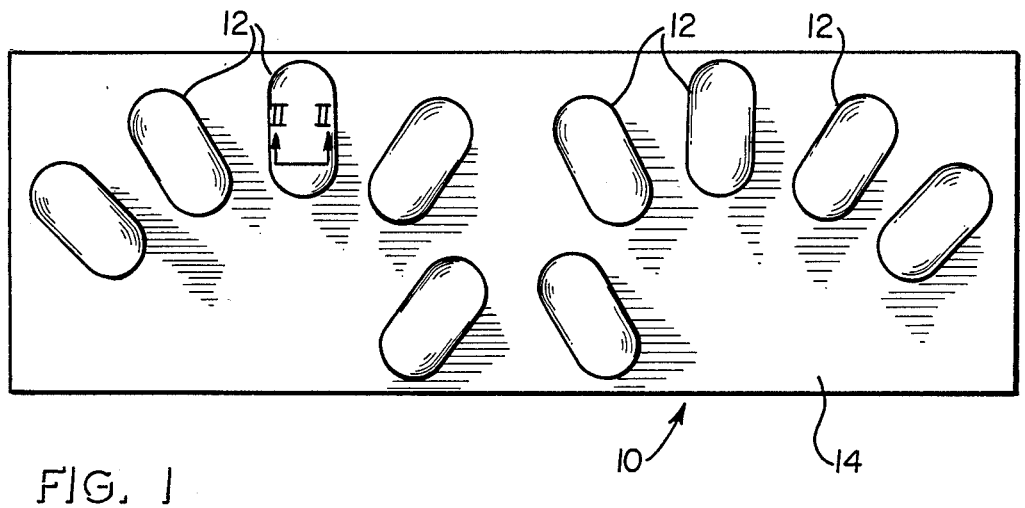
FIG. 1 illustrates a set of ten fingernail tapes, for human fingernail application, mounted on a release liner.
Figure 2:
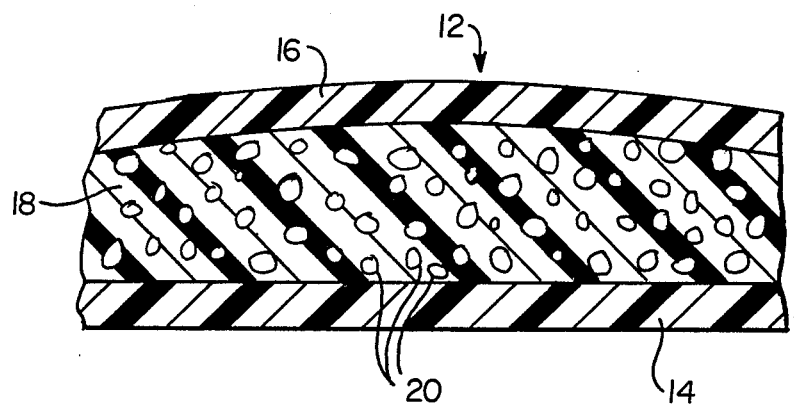
FIG. 2 is a sectional view through lines II—II of FIG. 1, illustrating the various layers of an embodiment of the present nail treatment device.

Referring now to FIG. 1, the substrate sheet films or tapes of the present invention are shown in a convenient, ready-to-use configuration including ten fingernail-shaped patches on a release liner. FIG. 2 illustrates a sectional view through lines II—II of FIG. 1, and shows the various layers of the embodiment of the nail treatment device shown in the Figures. Ten fingernail tapes 12 are shown in FIG. 1, mounted on a release liner 14, and the combination provides a convenient, ready-to-use kit.

In the embodiment of the present nail treatment device shown in FIG. 2, a polymeric sheet material 16 is backed with an adhesive layer 18 within which is dispersed an aqueous phospholipid composition 20, shown as dispersed particles throughout the adhesive layer 18. The combined polymeric sheet material 16 and associated adhesive layer 18 and aqueous phospholipid 20 are backed by the release liner 14. The combined elements 16, 18 and 20 peel away from the release liner 14 for use.

Various materials can be used in the manufacture of the present tapes. Although substrates of nearly any inert type have utility as the backing layer of the tape, this backing layer (not to be confused with the release liner on the opposite side of the laminate) is preferably a polymeric material. Accordingly, although the backing layer may comprise paper, paper-like or wood based substrates, metal or foil sheets or films, treated papers and the like, ordinarily and preferably the backing layer is the polymeric sheet material 16 as shown in FIGS. 1 and 2. The polymer may be selected from any of a number of sheet- or film-forming polymeric materials, including but not limited to polyurethanes, polyethylenes, polypropylenes, polyvinyl polymers, polyorganosiloxane compositions and the like. More preferably, however, the polymeric sheet material 12 comprises a moisture vapor permeable polymer such as urethane or polyurethane, so that the present nail tape does not deleteriously affect the moisture vapor transmission of the nail bed. The most preferred polymeric sheet material is a polyether polyurethane film having a thickness between about 2 and 50 mils.

The polymeric sheet material 12 provides a part of the vehicle by which an aqueous phospholipid composition (containing optional hydrolyzed animal protein) is held adjacent the surface of the human fingernail or toenail. Even the moisture vapor permeable polymeric sheet materials prevent rapid evaporation of water from the aqueous phospholipid, and so hold the aqueous phospholipid composition adjacent the nail bed throughout treatments of up to several hours. The aqueous phospholipid composition 20 may be one of a number of aqueous phospholipid compositions. Such compositions may comprise merely aqueous dispersions or solutions of phospholipids from various vegetable, animal or synthetic sources. The phospholipid of the present aqueous phospholipid composition is preferably a soya phospholipid, however, more preferably a granulated soybean lecithin phospholipid dispersed in water. For example, a commercial granular soybean lecithin (oil-free phosphatides with minimal to non-existent residual fiber sold under the trade name Centrolex® P(6240) may be incorporated in the present nail tapes. Centrolex® P(6240) is available from Central Soya, Chemurgy Division, 1300 Fort Wayne National Bank Building, Fort Wayne, Ind. 46802. This granulated soybean lecithin may be dispersed in water to form the preferred aqueous phospholipid composition of the present invention.

The preferred manner of applying the aqueous phospholipid composition to the nail bed comprises dispersing the aqueous phospholipid composition in a suitable pressure-sensitive adhesive, so that the adhesive may be adhered directly to the fingernail or toenail. In this embodiment of the invention, the adhesive provides the release matrix for the aqueous phospholipid composition dispersed therein. A wide variety of medically-acceptable pressure-sensitive adhesives may be used in the context of the present invention, and specific adhesives suitable for use include those pressure-sensitive adhesives prepared from acrylic emulsions such as the Rohm and Haas thermoplastic acrylic formulas sold under the trade designations Rhoplex N-560, Rhoplex N-580, Rhoplex N-582, Rhoplex N-619, Rhoplex N-1031 and Rhoplex LC-67. These thermoplastic acrylic polymers are characterized in part by their excellent adhesion to difficult substrates including polyolefins, their absence of need for tackifiers and their ability to resist delamination under wet conditions, crucial in the context of the present invention.

Upon lamination of the polymeric sheet material with the adhesive layer containing the aqueous phospholipid composition, the laminate is most useful when backed—on the opposite side from the polymeric sheet material—with a release liner. Release liners are generally well known in the art, and comprise paper or polymer sheets on which, on one side, has been deposited a release material. Release materials are those coatings or materials to which a wide variety of adhesives demonstrate only controlled minimal adherence. Typical release liners bear a smooth, glossy coating of polyorganosiloxane (silicone) on one side.

To use a nail tape according to the present invention, the user removes the tape 12 from its release liner 14, and applies it with moderate pressure to the surface of a clean, dry, unpolished nail. Release of aqueous phospholipid from the pressure-sensitive adhesive layer begins immediately, and therefore hydration of the keratinous matrix of the nail begins within a few minutes. Cosmetic and therapeutic benefit is accomplished by application of the nail tape for periods as short as a half-hour, but the tapes may also be left in position for several hours when convenient, usually at night, for full hydration of the fingernail or toenail. Hydration of the keratin of the fingernail or toenail prevents brittleness in the nail structure, and thus promotes avoidance of chipping, nail breakage, splitting, etc.

Various additives may be included in the adhesive layer 18 and/or the aqueous phospholipid composition 20, to improve properties, provide germicidal benefits, maintain integrity of the laminate structure, etc. For example, a bactericide or bacteriostat may be added to the aqueous phospholipid composition to arrest or reverse the growth of microorganisms, which the presence of the nutrient phospholipid might encourage. A typical broad-spectrum bacteriostat comprises one of the family of Germabens®, including Germaben II and Germaben II-E available from Sutton Laboratories, Inc., 116 Summit Avenue, Chattum, N.J. 07928. Germaben II, as an example, contains propylene glycol, diazolidinyl urea, methylparaben and propylparaben. Because Germaben II is readily soluble at levels of 1 percent in both aqueous solutions and oil-water emulsions, Germaben II is suitable for inclusion in the aqueous phospholipid compositions of the present invention. Other bacteriostats and preservatives known in the art may likewise be incorporated. However, germicides containing diazolidinyl urea are preferred for use on the nail bed due to their special suitability for controlling the normal fauna of the human nail and cuticle despite a phospholipid environment.

Included within the aqueous phospholipid composition may be optional hydrolyzed animal proteins, in amounts up to about 50% by weight of the aqueous phospholipid composition. These optional hydrolyzed animal proteins may include gelatins, collagen or elastin or other peptides or polypeptides. Hydrolyzed animal proteins can contribute to keratin integrity and thus have utility in the present device.

Dispersants and other additives to the compositions used to manufacture the present nail tapes are discussed further in the following Examples. Despite other minor formula differences between various compositions used in the preparation of the present nail patch, all nail patches are the same in that they contain adhesives which contain at least 15 percent phospholipid on a dry solids basis.

EXAMPLE I

A polymer modifier solution was prepared containing 20 parts by weight ammonium hydroxide, 56 parts by weight water and 14 parts by weight of a pale, high-softening-point, high-acid-number, thermal plastic resin. The thermal plastic resin used bore the trademark PENTALYN® 856 synthetic resin, available from Hercules Incorporated, Wilmington, Del. 19899. The PENTALYN® 856 synthetic resin is of the chemical family of diabasic acid-modified resin ethers. The PENTALYN® 856 synthetic resin is an amber solid or flake with a typical rosin odor.

The polymer modifier solution was given the working designation MD0174.

A second solution BR6462 was prepared containing 388 parts by weight water, 2 parts by weight of Germaben II and 100 parts by weight of Centrolex® P granular soybean lecithin. The total solids of BR6462 were 20 percent, inasmuch as Germaben II contains 50 percent solids by weight, and the 100 parts of Centrolex® P contains 97 percent by weight solids.

Using the above two solutions and other constituents, the adhesive layer for a nail tape was formulated by admixing 150.0 parts by weight Rhoplex N-560, 100.0 parts by weight Rhoplex N-580, 4.75 parts by weight MD0174, 175.0 parts by weight BR6462, 1.5 parts by weight of Cab-O-Sperse® with two separate pre-blends containing 1 part by weight water and 1 part by weight ammonium hydroxide, and 3.0 parts by weight water and 3.0 parts by weight ASE-60, respectively. Cab-0-Sperse ® is the trade name of an aqueous fumed silica dispersion, which is made from pure amorphous silica and which functions as a thickener and frictionizer in polymeric compositions. Cab-O-Sperse ® dispersions contain CAB-O-SIL ® fumed silica, which is a synthetic colloidal, amorphous silica produced by the hydrolysis of silicon tetrachloride vapor in a flame of hydrogen and oxygen. This method of silica manufacture results in a product having high external surface area, low density, low moisture content and a three-dimensional chain-like structure of the primary particle. ASE-60 is an aqueous acrylic emulsion which contains 28 percent solids by weight, has a pH of 3.5 and has a product viscosity of 10 centipoise. The constituents and amounts of the adhesive layer are summarized in Table I.

TABLE I

| Material | Concentration | Dry | Wet |
|---|---|---|---|
| Rhoplex N-560 | 55 | 82.5 | 150.0 |
| Rhoplex N-580 | 55 | 55.0 | 100.0 |
| MD0174 | 15.6 | 0.74 | 4.75 |
| BR6462 | 20 | 35.0 | 175.0 |
| Cab-O-Sperse ® | 12 | 0.225 | 1.5 |
| Water } Blend | | | 1.0 |
| Ammonium Hydroxide | | | 1.0 |
| Water } Blend | 28 | .84 | 3.0 |
| ASE-60 | | | 3.0 |
| | TS 39.7% | 174.305 | 438.85 |

The added constituents were emulsified in an Oakes mixer for 2 hours at medium speed (20 r.p.m.), yielding a product having a viscosity of 6400 centipoise.

A number of release liners were coated with the adhesive emulsion prepared above, using a knife-over-roll coater set at a 15–20 mil. gap. The coated liners were dried for 8 to 10 minutes at 200°–225° F. and were then laminated to a 10 mil. polyether polyurethane film using a 20 pound roller. Afterwards, an additional period of drying (2 minutes) at 200°–225° F. was completed. In order to assure a satisfactory adhesion of the adhesive to the polyether polyurethane film, the laminate was rolled again with the 20 pound roller.

The above adhesive emulsion was also coated directly onto polyether polyurethane films by the same knife-over-roll, set at 15–20 mil. gap. The films were dried for 10 minutes at 200°–225° F. The adhesive films laminated directly to the polyether polyurethane film accommodated a later-applied release liner without subsequent delamination, whereas the adhesive layer cast directly onto the release liner prior to curing demonstrated tight release, fish eyes and delamination of adhesive upon removal of the release liner. Direct deposition of the adhesive emulsion onto the polyethylene polyurethane film was selected as the preferred method for manufacturing the present nail tape. In addition, when the present nail treatment device was stamped from polyethylene polyurethane films onto which had been deposited the above adhesive composition, little or no adhesive residue was observed on the nail after the patch had been in place seven and one-half hours.

EXAMPLE II

The adhesive composition described in Example I was prepared except that the equal part dilution of the ammonium hydroxide and ASE-60 was eliminated prior to mixing. Small particles appeared in the adhesive composition, and it is believed that the undiluted addition of the ammonium hydroxide and the ASE-60 was responsible for the creation of the unwanted small particles. Dilution of the ammonium hydroxide and ASE-60 as described in Example I has consistently eliminated this problem.

EXAMPLE III

The adhesive composition according to Example I was prepared, except that the parts by weight of Centrolex ® P were increased from 1.5 to 1.9, for total parts by weight of 439.25. After the adhesive was laminated with polyether polyurethane film and cured, the adhesive layers according to this Example left even less or no adhesive residue on the human nail bed after seven and one-half hours' wear, than did the adhesive layer prepared in accordance with Example I.

EXAMPLE IV

The adhesive composition of Example III was prepared and deposited on an 8 mil. thick polyethylene polyurethane film, and after curing the laminate was mounted upon release liner number 8716, a trade designation of the supplier H. P. Smith. The release liner had the characteristics of 60 pounds per ream, 10 grams per inch release value, 60 MD/70CD (g) tear strength, 40 MD/25CD (g) tensile strength and a thickness of 3.4 mils. The above-identified release liner was found to result in fewer break lines than other release liners tested.

Although the invention has been described in the context of specific Examples, above, the invention is only to be limited insofar as is set forth in the accompanying claims. For example, alternate adhesives and germicides, preservatives or bacteriostats may be substituted for those disclosed herein. Furthermore, although it is ordinarily expedient that the aqueous phospholipid composition be dispersed within the adhesive layer, other physical configurations combining an adhesive layer and aqueous phospholipid composition are conceivable. For example, a single or plurality of thin layers of aqueous phospholipid can interleave the adhesive itself, or else interleave the area between the polymer backing and the adhesive layer, or interleave all of the areas including the spaces between the polymeric sheet material 16, the adhesive layer 18 and the release liner 14 of FIG. 2. As a further example, a layer of aqueous phospholipid could be retained in the commercial product between the adhesive layer 18 and the release liner 14, as long as the adhesive layer 18 were sufficiently deformable so as to suffuse around the aqueous phospholipid to create pockets of aqueous phospholipid held against the nail bed. These and other modifications do not affect the scope of the invention, set forth as follows.

We claim:

1. A device for application to the surface of a fingernail or toenail, comprising:
   a substrate sheet having an inner surface thereto;
   an aqueous phospholipid composition affixed adjacent said inner surface of said substrate sheet; and
   an adhesive layer comprising a pressure-sensitive adhesive layer affixed adjacent said inner surface of said substrate sheet; wherein said aqueous phospholipid composition is dispersed within said adhesive layer.

2. The device according to claim 1, wherein said substrate sheet further comprises a polymer sheet.

3. The device according to claim 2, wherein said polymer further comprises a moisture vapor permeable polymer.

4. The device according to claim 3, wherein said moisture vapor permeable polymer further comprises a polyethylene polyurethane polymer.

5. The device according to claim 1, wherein said aqueous phospholipid composition further comprises an aqueous soya phospholipid composition.

6. The device according to claim 5, wherein said aqueous soya phospholipid composition further comprises a dispersion of granulated soybean lecithin phospholipid in water.

7. The device according to claim 5, wherein said aqueous soya phospholipid composition is dispersed within said adhesive layer.

8. The device according to claim 7, wherein said aqueous soya phospholipid composition contains up to 50% by weight hydrolyzed animal protein.

9. The device according to claim 7, wherein at least 15% by weight of the combined aqueous soya phospholipid composition dispersed within said adhesive layer is phospholipid, on a dry solids basis.

10. The device according to claim 1, wherein said pressure-sensitive adhesive layer is further laminated with a release liner.

11. The device according to claim 10, wherein each element excluding the release liner conforms within the shape of a human fingernail.

12. The device according to claim 11, wherein each element excluding the release liner conforms within the shape of a human fingernail.

* * * * *